United States Patent [19]
Farley

[11] Patent Number: 4,733,663
[45] Date of Patent: Mar. 29, 1988

[54] MEDICAL INSTRUMENT FOR REMOVING BONE

[76] Inventor: Daniel K. Farley, 601 E. Lake Shore Dr., Barrington, Ill. 60010

[21] Appl. No.: 881,395

[22] Filed: Jul. 2, 1986

[51] Int. Cl.⁴ ............................................. A61B 17/16
[52] U.S. Cl. ..................................... 128/312; 128/305; 128/319; 30/278
[58] Field of Search ............... 128/312, 311, 305, 319, 128/305.3; 30/179, 173, 278, 280

[56] References Cited

U.S. PATENT DOCUMENTS

| | | | |
|---|---|---|---|
| 2,709,298 | 5/1955 | Mater | 30/173 |
| 3,936,935 | 2/1976 | Gregory | 30/179 |
| 4,201,213 | 5/1980 | Townsend | 128/312 |
| 4,513,745 | 4/1985 | Amoils | 128/305 |
| 4,530,356 | 7/1985 | Helfgott | 128/305 |
| 4,559,041 | 12/1985 | Razi | 128/305 |

*Primary Examiner*—C. Fred Rosenbaum
*Assistant Examiner*—Denise Whelton
*Attorney, Agent, or Firm*—Allegretti, Newitt, Witcoff & McAndrews, Ltd.

[57] ABSTRACT

There is provided an improved rongeur having a jaw mechanism comprised of a barrel member having a honed cutting edge on one extremity thereof and having a shaft member located within and arranged for reciprocal motion. On the shaft member there is provided a plate member attached at one extremity to trap bone against the cutting edge. A lever mechanism is provided having paired handle levers joined by a pivot and having the barrel and shaft member attached to the handle levers between the handle portion and the pivot. On the shaft member there is further provided a cavity arranged to slide within the barrel progressively as the cutting operation proceeds, gradually drawing severed bone within the capturing cavity. Stop surfaces are located in the cutting area at a position relative to the cutting edge to avoid direct force contact on the cutting edge when the shaft member is reciprocated to its full extent within the barrel member.

9 Claims, 8 Drawing Figures

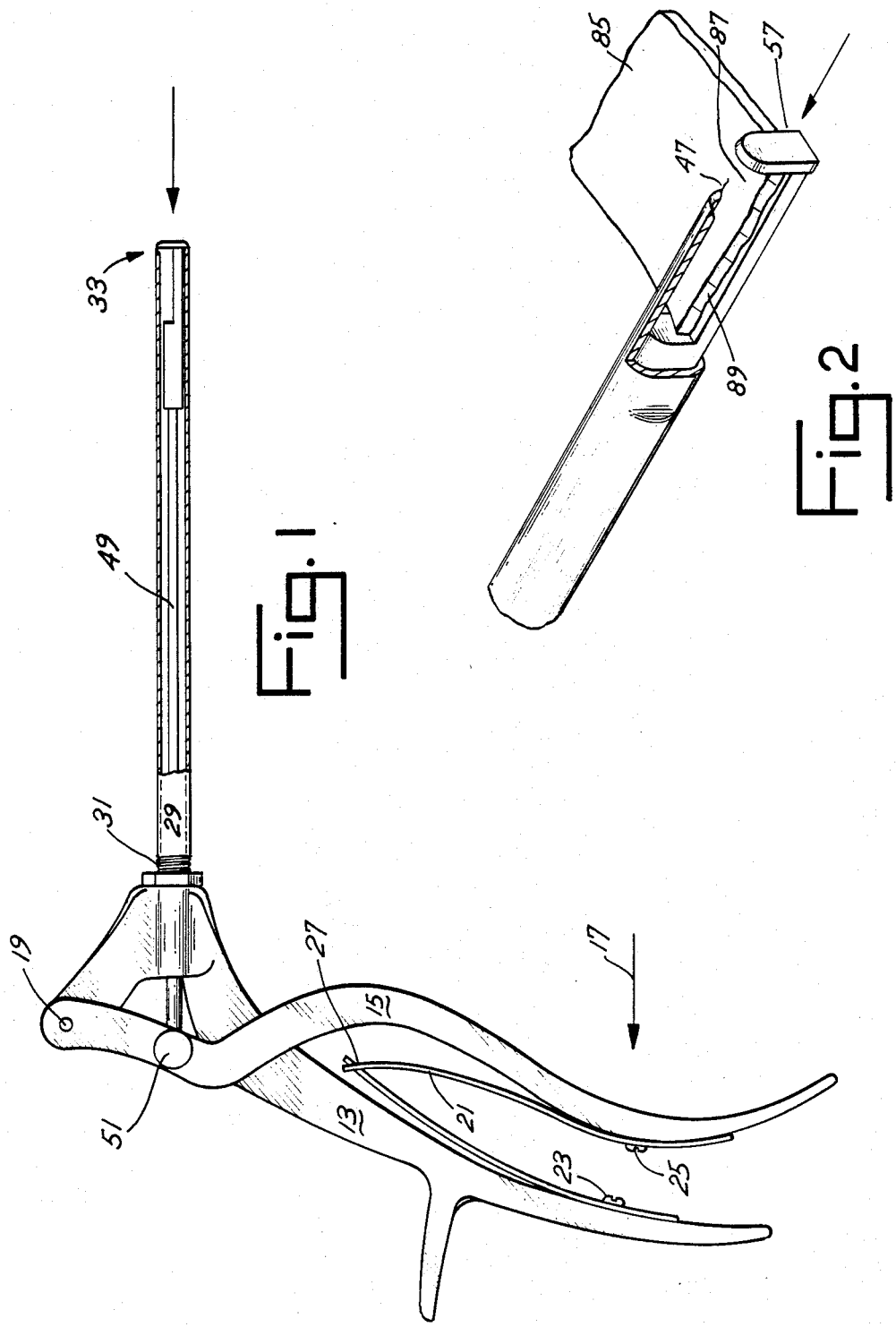

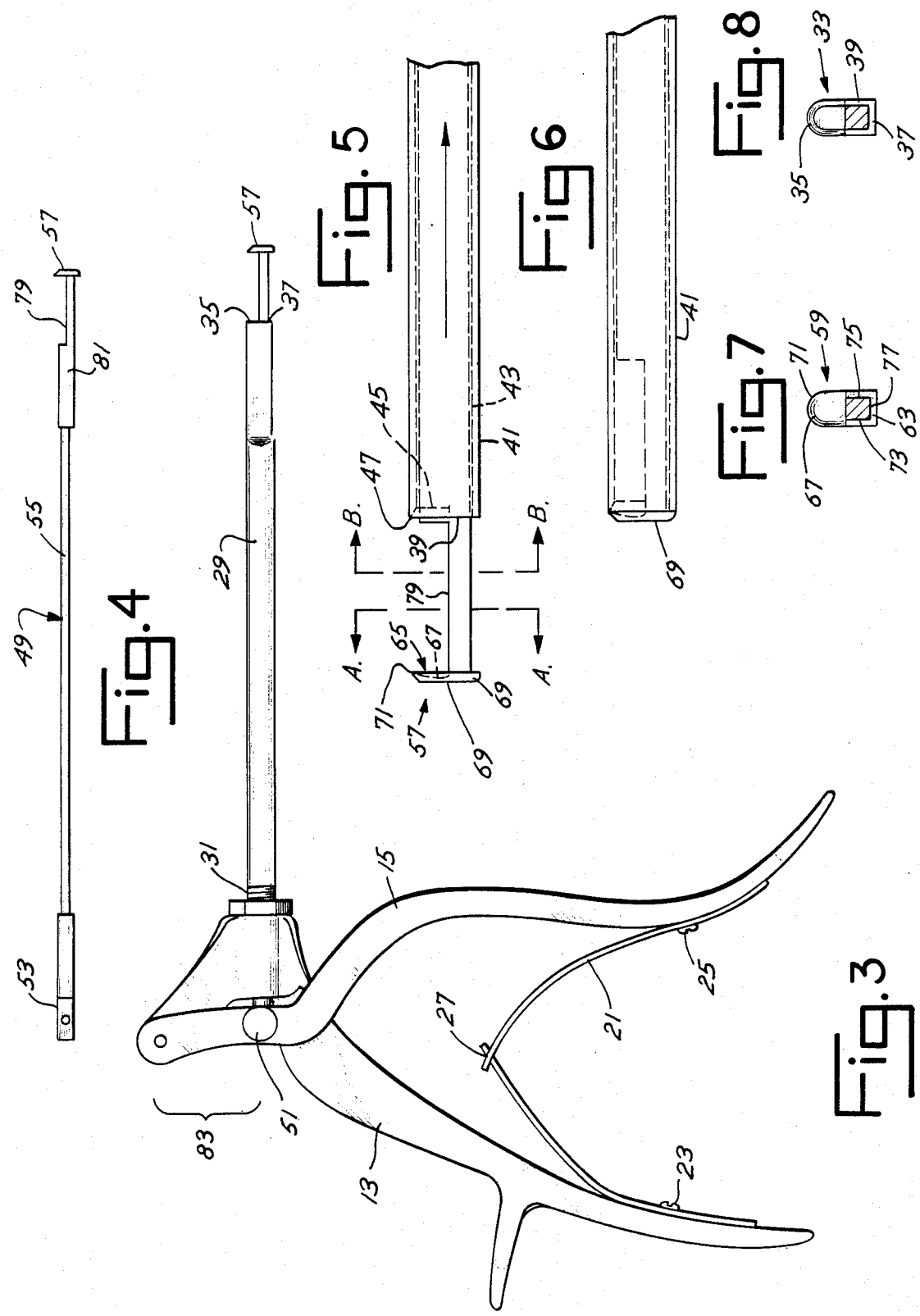

MEDICAL INSTRUMENT FOR REMOVING BONE

RELATED APPLICATION

This application is related to U.S. patent application Ser. No. 560,210, filed Dec. 12, 1983, naming inventors Dale W. Wright and David W. Wright, which is assigned to the same assignee as the present application.

BACKGROUND OF THE INVENTION

This invention relates to forceps of the rongeur or bone cutting type and more particularly to a rongeur structure which prevents premature ware in the bone cutting surfaces.

It has long been an object in the art to provide simple, inexpensive forceps capable of easy disassembly and cleaning, and most importantly capable of safe and efficient operation. Prior patents issued in this art have proposed possible solutions. Typical of the prior art is the patent issued to De Vilbiss, U.S. Pat. No. 1,040,523, which provides a lever mechanism comprising a handle having two sides arranged to pivot towards one another about a central axis. On extensions of these handle members there is provided a jaw mechanism comprising a first movable jaw arranged to travel within a slot defined within a second movable jaw. Bone seized between the jaws is pulled within the slot as it is cut.

A problem associated with this and other mechanisms in the art is that uncontrolled force is applied to the bone surface surrounding the cutting area, such that possible bone breakage and splintering may occur. If operating near the spinal cord, possible nerve damage may result. Further, bone chips cut from the bone structure are not well contained by the instrument and contamination of the wound may result. Finally, with the pivot placed between the jaw mechanism and the lever handles limited mechanical advantage is available, making the instrument tiring to use. Further, the large force applied to the bone may also be applied across the cutting surfaces which come into contact with each other at the end of the cutting stroke. Such large forces applied across contacting cutting surfaces cause unnecessary waring of the sharp edges.

Accordingly, it is the primary aim of the present invention to provide an approved forcep or rongeur for cutting bone wherein the bone chips, once severed, are safely contained within the instrument and held therein until selectively ejected, and the force applied between meeting cutting surfaces is decreased at the end of the cutting stroke in order to prevent ware thereto.

It is also an object of the present invention to eliminate uncontrolled forces in and about the cutting area to avoid possible bone breakage and splintering beyond the cutting area while utilizing structure which prevents excessive ware on the cutting surfaces.

It is also an object of the present invention to modify the mechanical leverage to provide improved mechanical advantage for the device and to provide better control during operation while utilizing structure which prevents excess ware on cutting surfaces located in the cutting area.

SUMMARY OF THE INVENTION

These and other objects of the invention are accomplished in an improved forcep or rongeur having a jaw mechanism comprised of a barrel member having a first cutting surface on one extremity thereof and having a shaft member located within and arranged for reciprocal motion within the barrel member. On the shaft member there is provided a plate member attached at one extremity and having a second cutting surface to trap bone against the first cutting surface of the barrel member. On the shaft member there is further provided a cavity arranged to slide within the barrel progressively as the cutting operation proceeds, gradually drawing severed bone within the capturing cavity, allowing for a cutting action rather than a crushing action, thereby relieving pressure on the plate member and thus reducing the possibility of breaking said member while cutting bone structures.

Other objects and advantages of the invention will become apparent upon reading the following detailed description and upoon reference to the drawings.

DESCRIPTION OF THE DRAWINGS

FIG. 1 is a side view partially cut away of a preferred embodiment of a rongeur of the present invention.

FIG. 2 is an enlarged perspective view of the distal end of the rongeur of FIG. 2 in operation.

FIG. 3 is a side view of the rongeur of FIG. 1.

FIG. 4 is a side view of a shaft member on the rongeur of FIG. 1.

FIG. 5 is a side view of the end of the barrel member of the rongeur of FIG. 1, showing the shaft member in its open position.

FIG. 6 is a side view of the end of the barrel member of the rongeur of FIG. 1, showing the shaft member in its closed position.

FIG. 7 is a cross-sectional view of the end of the shaft member taken along line AA of FIG. 5.

FIG. 8 is a cross-sectional view of the end of the shaft member taken along line BB of FIG. 5.

DESCRIPTION OF THE PREFERRED EMBODIMENT

Referring to FIG. 1, a rongeur 11 includes a pair of handle members 13, 15 arranged to be held within the human hand and pulled together in the direction of an arrow 17 much in the same manner as a pair of pliers. Handle members 13, 15 are arranged to pivot about an axis 19 and each handle is arranged as shown in the drawing to support and actuate a barrel member and a shaft cutting mechanism as more fully described below.

A squeezing force on the handle members closes the handles in the direction of arrow 17, and concurrently compresses an intermediate spring 21 located between the handle members. This generates a returning force to return the handles to their starting position as shown in FIG. 3. The return spring is typically formed of spring steel made of two distinct and separate members, each rigidly attached to respective individual handle members at lower extremity points 23, 25 respectively, while being hingedly interlocked at an intermediate contacting point 27.

A barrel member 29 is rigidly attached by screw threads 31 to handle member 13. Barrel member 29 is formed of a cylindrical tube but having its distal end (as shown in FIGS. 2 and 5) formed of a uniform cross-section shape being somewhat rectangular and formed of three straight sides and a protruding or curved fourth side, as shown in FIG. 8. Barrel member 29 has external threads 31 at its point of attachment to the handle, and has at its other extremity a work area 33 which includes a cutting surface 35 and a stop surface 37 (more clearly shown in FIG. 8). Cutting surface 35 and stop surface 37 are formed from the end edge 39 of the barrel member. The upper portion of end edge 39 is honed to form cutting surface 35 and the lower portion of the end edge 39 is formed flat to provide stop surface 37.

As shown in FIG. 5, barrel member 29 includes an outside face 41, forming the outer surface of the barrel member, and an inside face 43 spaced from the outside face and defining the containing area of the barrel member. Cutting surface 35 is formed from a bevel surface extending between the inside face (at 45) and the outside face of the barrel member. The intersection of the bevel surface and the outside face provides a cutting edge 47.

Mounted for reciprocal motion within the barrel there is provided a shaft member 49 (FIG. 1) pivotally attached at an axis 51 to handle member 15 and arranged to selectively protrude from the barrel at its other extremity. As shown in FIG. 4, shaft member 49 is comprised of a first attachment portion 53 for connection to the pivot mount at handle 15, and a central force transmission portion 55 for transmitting the force of the handle leverage mechanism remotely to the site of the bone cutting at the distal end of the barrel. Finally, there is a bone cutting and trapping portion comprised of a plate or foot 57 mounted transversely to the distal end of the shaft.

As shown in FIGS. 5 and 7, plate member 57 includes a work area 59 which includes a cutting surface 71 and a stop surface 63. Cutting surface 71 and stop surface 63 are formed from the inside face 65 of the plate member which confronts end edge 39 of the barrel member.

The upper portion of inside face 65 includes a cavity 67 shaped into the plate member to form the cutting surface 61. An outside face 69 of the plate member forms the outer surface of the sides and end of the plate member. The surface defining cavity 67 intersects a portion of the outside face 69 forming a cutting edge 71.

The lower portion of inside face 65 seats the distal end of shaft member 49, which may be secured or formed integral to plate member 57. As shown in FIG. 7, the cross-sectional shape of the distal end of shaft member 49 is square and the end is secured to plate member 57 in a location to leave portions of inside face 65 at the sides 73, 75 and bottom 77 of the shaft member. These portions of inside face 65 are formed flat to provide stop surface 63.

Within shaft 49 there is provided a cavity portion 79 (see FIGS. 4 and 5). Cavity portion 79 is formed by a flat depression or notch represented by a cut away portion of the shaft. The inside face of plate member 57 forms one end of cavity portion 79 and the other end is formed by a sealing portion 81 (FIG. 4). Sealing portion 81 is provided to close the gap between the barrel and the shaft as the shaft end is drawn into the barrel. This sealing portion acts to maintain the barrel free of debris and serves to eject bone fragment following a cutting sequence.

To improve the mechanical advantage of the forceps, increased leverage is provided by attaching the barrel and shaft between the handle pivot and the handle grasping portion where hand pressure is applied during the squeeze. By varying the distance 83 (FIG. 3) between the barrel and shaft attachment points and the pivot, mechanical advantage can be set to provide comfortable operation during strenuous bone cutting procedures. Additionally, the tendency of the forceps to move during actuation is reduced as the spacing 83 is increased while fine control is retained by keeping the grasped portion of the handle near the barrel and shaft attachment.

In operation (see FIG. 2) a bone segment 85 with an unsevered portion 87 is trapped between the shaft and plate 57 and the cutting edge 47 of the barrel. As the shaft is drawn into the barrel, severed bone 89 is captured within the barrel. Once the stroke has been completed the forceps are removed from the cutting site, inverted, and the shaft extended from the barrel to facilitate deposit of the severed bone into the proper receptacle.

When the shaft member is reciprocated to its full extent, as shown in FIG. 6, stop surface 37 of the barrel member and stop surface 63 of the plate member make full contact stopping the extent of reciprocation of the shaft member. At this point in the reciprocation, the two stop surfaces 37, 63 carry the full direct force applied to the handle members. Cutting edge 47 of the barrel member and the cutting edge 71 of the plate member are located relative to their associated stop surfaces 37, 63, respectively, so that cutting edges 47, 71 barely contact one another or, in fact, avoid contacting one another. This locating of the cutting edges avoids direct force contact of the cutting edges when the shaft member is reciprocated to its full extent. A major part of the totality of the force applied on the handles is applied to the stop surfaces. This prevents the sharp cutting edges 47, 71 from unnecessary waring.

While we have shown a presently preferred embodiment of the present invention, it will be apparent to those skilled in the art that the invention may be otherwise embodied within the scope of the appended claims.

What is claimed is:

1. A medical instrument for cutting and removing bone comprising:

a stationary tubular barrel member having a proximal end and distal end, wherein said distal end comprises a first working area, said first working area including a first cutting surface and a first stop surface, said first cutting surface and said first stop surface formed on opposite sides of the perimeter of said distal end wherein both said surfaces lie within a first plane substantially perpendicular to the axis of said tubular member, a solid cylindrical shaft member positioned coaxially within said barrel and arranged for reciprocal motion therein, said shaft member having a distal end and a proximal end, including a recess formed adjacent said distal end, said shaft member further comprising a plate member having a perimeter which is sized to substantially mate with the circumference of said barrel member to close said barrel member when said shaft member is reciprocated into said barrel, said plate member having a second work area, said second work area comprising a second cutting surface and a second stop surface, said second cutting surface and said second stop surface on the proximal face of said plate member formed on opposite sides of the perimeter thereof, said second cutting surface being formed by a concavity in the proximal face of said plate member such that both said second plane perpendicular to the axis of said shaft member, said first plane and said second plane being substantially parallel such that said first and second stop surfaces are in face confronting relationship and make full contact when said slidable shaft member is reciprocated to its full extent with respect to said barrel member, said full contact stopping the extent of reciprocation of said shaft member such that said first and second cutting surfaces are disposed in a cutting relationship while substantially avoiding direct force contact when said slidable shaft member is reciprocated to its full extent within said barrel member, and a lever means attached to the proximal end of both said barrel member and said shaft member for reciprocally translating said slidable shaft member within said barrel member causing said second working area associated with said slidable shaft member to reciprocate with respect to said first working area associated with said barrel member, thereby biting and severing any said bone positioned in the recess between said first and second cutting surfaces and causing both said severed bone and said recess to reciprocate into said barrel thereby capturing bone severed by said cutting surfaces within said recess.

2. A medical instrument according to claim 1 wherein said first cutting surface is a first cutting edge.

3. A medical instrument according to claim 2 wherein said second cutting surface is a cutting edge.

4. A medical instrument according to claim 2 wherein said stationary tubular barrel member includes an outside face forming the outer surface of said stationary tubular barrel member and an outside face spaced from said outside face and defining the containing area of said stationary tubular member, said first cutting surface including: a first cutting edge disposed on said outside face at a first portion of the extremity thereof; and a bevel surface extending between said first cutting edge and said inside face of said barrel member.

5. A medical instrument according to claim 4 wherein said first stop surface is formed of a flat surface extending between a second portion of the extremity of said outside face and said inside face of said stationary tubular barrel member.

6. A medical instrument according to claim 5, wherein said stop surface is orthogonal to said outside face.

7. A medical instrument according to claim 6 wherein said stationary tubular barrel member includes a uniform cross-sectional shape at said one extremity of said barrel member, said shape being somewhat rectangular formed of three straight sides and a protruding curved fourth side.

8. A medical instrument according to claim 7 wherein said first cutting edge is disposed on said protruding curved fourth cross section of said stationary tubular barrel member.

9. A medical instrument according to claim 1 wherein when said shaft member has been reciprocated to its full extent within said barrel member, said first and second stop surfaces make full contact and said first and second cutting surfaces do not make full contact.

* * * * *